US005599555A

United States Patent [19]
El-Nokaly

[11] Patent Number: 5,599,555
[45] Date of Patent: Feb. 4, 1997

[54] ENCAPSULATED COMETIC COMPOSITIONS

[75] Inventor: Magda El-Nokaly, Hamilton, Ohio

[73] Assignee: The Procter & Gamble Company, Cincinnati, Ohio

[21] Appl. No.: 999,435

[22] Filed: Dec. 17, 1992

Related U.S. Application Data

[62] Division of Ser. No. 673,879, Mar. 22, 1991, Pat. No. 5,215,757.

[51] Int. Cl.$^6$ .............................. A61K 9/14; A61K 47/00
[52] U.S. Cl. ..................... 424/488; 424/493; 424/494; 514/777; 514/781
[58] Field of Search ........................... 424/49, 488, 493, 424/494, 495; 514/777, 781, 171, 182, 170, 180; 252/299.01

[56] References Cited

U.S. PATENT DOCUMENTS

| | | | |
|---|---|---|---|
| 3,529,156 | 9/1970 | Fergason et al. | 250/83 |
| 3,576,761 | 4/1971 | Davis | 252/408 |
| 3,957,971 | 5/1976 | Oleniacz | 424/70 |
| 3,998,860 | 12/1976 | Brown et al. | 260/397.2 |
| 4,226,890 | 10/1980 | Howard | 426/92 |
| 4,301,023 | 11/1981 | Schuberth et al. | 252/299.7 |
| 4,378,381 | 3/1983 | Turbak et al. | 426/570 |
| 4,981,709 | 1/1991 | Furcsik et al. | 426/565 |
| 4,999,348 | 3/1991 | Cloca et al. | 514/182 |
| 5,106,644 | 4/1992 | El-Nokaly | 426/603 |
| 5,153,230 | 10/1992 | Jaffery | 514/873 |
| 5,156,766 | 10/1992 | Behan et al. | 424/450 |
| 5,157,046 | 10/1992 | Van Wauwe et al. | 514/397 |
| 5,215,757 | 6/1993 | El-Nokaly | 424/488 |

FOREIGN PATENT DOCUMENTS

| | | |
|---|---|---|
| 53-082505 | 7/1978 | Japan . |
| 56-032342 | 3/1981 | Japan . |
| 56-109966 | 7/1981 | Japan . |
| 59-072174 | 4/1984 | Japan . |
| 59-072173 | 4/1984 | Japan . |
| 59-181680 | 8/1984 | Japan . |
| 61281182 | 12/1986 | Japan . |
| 1346756 | 2/1974 | United Kingdom . |

OTHER PUBLICATIONS

Edward Sagavin, Cosmetics Science and Technology Interscience Publishers, New York, N.Y., 1957, pp. 236–239.
Derwent Publications, Abstract 4212C/24 of J 55/009655 1980.
Derwent Publications, Abstract 16492B/09 of J 54/006883 no date available.
Derwent Publications, Abstract 87–089962/13 of J 62/039686 no date available.
Derwent Publications, Abstract 37461 of J 57/147576 1982.
Brown et al., Liquid Crystals & Biological Structures, Academic Press (New York, 1979) 4–6, 14–17.
Gray, Molecular Structure and the Properties of Liquid Crystals, (Academic Press, 1962) 5–13, 39–54.
Saeda, Liquid Crystals, (M. Dekker, 1979) 99–162.
Hennock et al, "Effect of Xanthan Gum on the Rheology and Stability of Oil–Water Emulsions", J. Food Sci., vol. 49, No. 5, pp. 1271–1274 (1984).
Hitaka, "Food Emulsifiers –Liquid Crystals and Phase Diagrams", Yushi, vol. 37 No. 8, pp. 66–70 (1984).
Ganz, "Some Effects of Gums Derived from Cellulose on the Texture of Foods", Cereal Sci. Today, vol. 18, No. 12, pp. 398–403, 415, 416 (1973).e
Moore, "Nongelling Microcrystalline Cellulose Offers Superior Texture to Heat Sensitive Liquid Emulsions", Food Product Dev., vol. 12, No. 6 p. 38 (1978).
Hemkar, "Associative Structures of Polyglycerol Esters in Food Emulsions", JAOCS, Feb. 1981, pp. 114–119.
Kamide, et al., "Formation of Lyotropic Liquid Crystals of Cellulose Derivatives Dissolved in Inorganic Acids", Polymer Journal, vol. 18, No. 3, pp. 273–276 (1986).
Werbowyi, et al., "Liquid Crystalline Structure in Aqueous Hydroxypropyl Cellulose Solutions", Mol. Cryst. Liq. Cryst., vol. 34, pp. 97–103 (1976).
Bheda, et al., "Phase Behavior and Structure of Liquid Crystalline Solutions of Cellulose Derivatives", Colloid & Polymer Sci., vol. 258, No. 12, pp. 1335–1342 (1980).
Gray, "Chemical Characteristics of Cellulose Liquid Crystals", Faraday Diss. Discuss. Chem. Soc., vol. 79, pp. 257–264 (1985).
Bheda et al., "Cellulose Derivative Liquid Crystals and Their Application", Tech. Pap. Reg. Tech. Conf. –Soc. Plast. Eng. pp. 321–323 (1980).
Salamone, et al. "Xanthan Gum –A Lyotropic, Liquid Crystalline Polymer and Its Properties as a Suspending Agent", Soc. Pet. Eng. J. vol. 22, No. 4, pp. 555–556 (1982).
Glicksman, "Food Hydrocolloids", CRC Press, Inc. vol. 1 (1982).
Marchessault et al., (Nature, 184, 632, 633 (1956).
Chanzy and Peguy, J. Polymer Sci., 18, 1137–1144 (Polymer Physics Edition, 1980).
Conio, et al., J. Polymer Sci., 22, 273–277 (Polymer Letters Edition, 1984). pp. 78–93.
Fortin, et al., Macromolecules, 22, (5) 2286–2292 (1989).

Primary Examiner—Ralph J. Gitomer
Attorney, Agent, or Firm—John M. Howell; Jerry J. Yetter; Rose Ann Dabek

[57] ABSTRACT

This invention relates to polymeric liquid crystals prepared from a polysaccharide and a solvent, preferably water, which are used to deliver nutrients, perfumes, flavors, drugs and other ingredients in foods, cosmetics, household soaps, health care products e.g. bar or liquid soaps, toothpaste, shampoos, creams, and lotions and other preparations. The encapsulated active vehicle comprises:

(a) from about 0.001% to about 60% of an active; and
(b) from about 40% to about 99.999% of a stable polymeric liquid crystal consisting essentially of:
  (1) from about 10% to about 90% of a solvent; and
  (2) from about 10% to about 90% of a polysaccharide having a molecular weight of from about 500 to about 1,000,000.

18 Claims, No Drawings

ENCAPSULATED COMETIC COMPOSITIONS

This Application is a divisional Application of Ser. No. 07/673,879, filed on Mar. 22, 1991 now U.S. Pat. No. 5,215,757.

FIELD OF THE INVENTION

This invention relates to polymeric liquid crystals prepared from a polysaccharide and a solvent, preferably water, which are used to deliver nutrients, perfumes, flavors, drugs and other ingredients in foods, cosmetics, soaps, and other preparations.

BACKGROUND OF THE INVENTION

It has now been discovered that polymer liquid crystals such as polysaccharide liquid crystals can be made to encapsulate and deliver nutrients such as vitamins, minerals, or flavors to foods; sunscreens, emollients, antiseptics, perfumes, hair or skin care ingredients to health care products e.g. soaps, toothpaste, shampoos, creams, and lotions.

The liquid crystalline state exists between the boundaries of the solid phase and the isotropic liquid phase (i.e. an intermediate between the three dimensionally ordered crystalline state and the disordered dissolved state). In this state some of the molecular order characteristics of the solid phase are retained in the liquid state because of the molecular structure and short range intermolecular interaction. The ability of some compounds to form a liquid crystalline mesophase had been observed nearly a century ago. Since that time many compounds exhibiting liquid crystalline properties have been synthesized. D. Sek: Structural variations of liquid crystalline polymer macromolecules; *Acta Polymerica*, 39 (1988) No. 11, p. 599.

Low molecular weight organic surface active compounds (emulsifiers) are distinguished from polymers. The latter comprise large molecules made up of repeating units while the former are low molecular weight compounds. Physically and chemically, these two subclasses of materials are different from each other.

Low molecular weight liquid crystals, i.e. liquid crystals formed from a low molecular weight emulsifier or organic amphiphile (a compound having both a polar and a non-polar group, as a soap, lecithins or long chain fatty acid monoglyceride) are known to encapsulate and act as a delivery vehicle for drugs, flavors, nutrients and other compounds. Because of their weight, they are added at higher concentrations to achieve the same functionality as polymer liquid crystals which are made of a polymer and a solvent. The polymers can be a long chain of repeating units of amphiphiles or polymerized low molecular weight materials. They also form different types of liquid crystals.

Amphiphile molecules contain both hydrophilic and lipophilic grouping. They are substances exhibiting a marked tendency to adsorb at a surface or interface. Thus, surfactants are amphiphilic molecules divided into nonionic (no charge), ionic anionic (negative charge) and cationic (positive charge) and amphoteric (both charges) based on whether or not they ionize in aqueous media. Surfactants are also commonly called emulsifying agents. They are usually classified as lipids, which are fat-like substances. Surfactants are monomers (one structural unit), and are derived from natural oils and fats and crude oils.

The polymers of this invention are polysaccharides. They belong under the general group of carbohydrates, in contrast to surfactants or lipids. Carbohydrates are polyhydroxy compounds of the general formula $(CH_2O)n$, of which glucose (glu) is an example. Polysaccharides are carbohydrates derived from monosaccharides by the removal of n−1 molecules of water from n-molecules of monosaccharides. In polysaccharides, sugar monomers repeat, i.e. Glu-(Glu)$_n$-Glu-. Gums, fibers and hydrocolloids also may be classified as polysaccharides. They can be natural, biosynthetic, or modified. Their origin can be plant or microbial polysaccharides. Because polysaccharides are all compounds of higher molecular weight, they have the properties generally associated with colloids.

In the literature, liquid crystals are also referred to as anisotropic fluids, a fourth state of matter, polymer association structure or mesophases. Those terms are used interchangeably. The term "polymer liquid crystals" as used herein means "polymeric lyotropic liquid crystals" unless otherwise specified. The term "lyotropic" means a liquid crystalline system containing a solvent. This type of liquid crystal is distinguished in the art from thermotropic, heat or magnetically induced, liquid crystals. The same compound can form lyotropic and thermotropic liquid crystals.

A general description of the phase behavior of a soluble polymer in a solvent is as follows: (I) The polymer dissolves in the solvent to form an isotropic polymeric solution. (II) When the concentration of the polymer increases, a biphasic region which is a mixture of isotropic polymeric solution+liquid crystals is formed. (III) When the level of the polymer increases further and the required mixing is applied, a homogeneous single-phase liquid crystal range is induced. (IV) When even more polymer is present, a mixture of liquid crystals and crystalline polymer forms. (V) When extremely large amounts of polymer are present a crystalline and/or partially crystalline phase are present.

It is important to understand that liquid crystals are substances that possess mechanical properties resembling those of fluids yet are capable of transmitting polarized light (birefringence) under static conditions. In some cases they may show Bragg reflections characteristic of a well-defined molecular spacing. They have high degrees of orientational order and chain extensions.

Polymeric lyotroptc liquid crystals are subdivided into three subclasses: I. nematic, II. cholesteric, and III. smectic, which are optically anisotropic. See J. H. Wendorff, in "*Scattering in Liquid Crystalline Polymer Systems*" in "*Liquid Crystalline Order in Polymers*," A. Blumstein (ed.), Academic Press, Chapter 1 (1978).

I. In the nematic liquid crystalline phase the centers of gravity of the polymeric particles are arranged at random, consequently no positional long range order exists. Within volume elements of a macroscopic sample, the axes of all particles are oriented in a specific direction. Near the smectic-nematic transition temperature, there may be an additional ordering (positional order).

II. The cholesteric liquid crystalline phase is often thought of as a modification of a nematic phase, since its molecular structure is assumed to be similar to the latter. No positional order but only an orientational order exists in the cholesteric phase. In contrast, however, to the nematic phase, the cholesteric phase is characterized by the fact that the direction of the long axes of the molecules change continuously within the sample. This leads to a twist about an axis perpendicular to the long axes of the molecule.

III. In the smectic phases the centers of gravity of the elongated molecules are arranged in equidistant planes and smectic layers are formed. The planes are allowed to move perpendicularly to the layer normal and within the layers different arrangements of the molecules are possible. The long axes of the molecules can be parallel, normal or tilted with respect to the layer. A two-dimensional short range order or a two-dimensional long range order can exist within the smectic layers. The smectic modifications are labeled according to the arrangement of the particles within the layers.

Investigations of miscibility between different liquid crystalline modifications allow the distinction between various smectic phases and between smectic, cholesteric and nematic phases.

The light microscopy of liquid crystals is described in *The Microscopy of Liquid Crystals*, Norman Hartshorne, Microscopy Publications, Ltd., Chicago, Ill., U.S.A., 1974. Birefringence occurs in general for mesomorphic states. Methods for microscopic observation and evaluation are discussed in Chapter 1, pp.1–20, and cholesteric mesophase (liquid crystal) systems are discussed in Chapter 6, pp. 79–90. A preferred method for determining occurrence of liquid crystals is by observing birefringence of thin liquid crystal films between glass slides or from thin slices of a material under a polarizing microscope.

Focusing on the polymeric lyotropic liquid crystals of the present invention, in general, they are prepared by mixing the polymer with a sufficient amount of a solvent within the critical concentration and temperature ranges. The polymeric liquid crystalline phase flows under shear and is characterized by a viscosity that is significantly different from the viscosity of its isotropic solution phase. In other words, for some polymers, as the concentration increases, the viscosities of the polymer/solvent mixture increases until it reaches a viscosity peak. Then the viscosity decreases dramatically. The presence of such viscosity peaks signifies the onset of, or the presence of, a polymeric lyotropic liquid crystalline order. Hence, liquid crystals are distinguishable from polymeric systems which are isotropic solutions, pure solids, simple mixtures of solids and liquids and rigid isotropic polymeric gels. Rigid gels do not flow under shear like liquid crystals. Also, when viewed with a polarized light microscope, liquid crystals show identifiable birefringence, as, for example, planar lamellar birefringence, whereas when isotropic solutions and rigid gels are viewed under polarized light, both show dark fields.

Liquid crystal xanthan gum (a polymer) is reported to stabilize an oil-in-water emulsion (Biological Abstract 79:12413, Food Research Institute, Norwich, U.K. and M. Hennock et al., *J. Food Sci.*, 49,1271, (1984).

Adding isotropic solutions of the polysaccharide in polar solvent to a fat, oil or other hydrophobic medium would lead to unacceptable results. If the polysaccharide were soluble in the solvent, the solvent nevertheless would not mix well with the medium. The solution would be expected to separate from the fat during storage or use. Flowable polysaccharide liquid crystals, on the other hand, allow substantial amounts of polysaccharide to be incorporated into a hydrophopic medium. Such mixtures can substitute for fats or oils in a variety of edible, fat-containing products without suffering the drawbacks of nonliquid crystal technology, i.e. gritty taste, and in both edible and non-edible products without separation or syneresis.

It is particularly desirable that the delivery vehicle composition be made from ingredients that are presently used and approved for use in edible product applications and for applying to the skin.

It is also an object of this invention to provide an encapsulating system to the food without affecting the mouth feel and taste of the product.

It is also an object of this invention to provide an encapsulating system which can be made with a minimum of processing and which is easily mixed with the food.

It has now been found that the above objects, as well as other benefits, can be attained by substituting liquid crystals formed from polysaccharides and solvents for conventional encapsulating agents, e.g. dextrins, gels, high melting fats, etc. present in certain foods and household items.

SUMMARY OF THE INVENTION

The present invention relates to a delivery vehicle for nutrients, flavors, perfumes, drugs, health and beauty care ingredients and other actives comprising:

(a) from 0.001% to about 60% of an active;
(b) from about 99.99% to about 40% of a stable polymeric liquid crystal consisting essentially of:
  (1) from about 10% to about 90% of a solvent; and
  (2) from about 10% to about 90% of a polysaccharide having a molecular weight of from about 500 to about 1,000,000.

Without intending to necessarily limit the scope of the invention, it is believed that the polymeric polysaccharide liquid crystal adsorbs onto solid/liquid, solid/gas, liquid/gas or liquid/liquid interfaces in heterogeneous systems such as solid fats in shortening, solid surfactant or oils in skin or hair creams, or solids in drug tablets (liquid/solid) and on air bubbles in frostings, mousses, cakes, leavened baked goods. Dentifrices, shampoos, lotions, and conditioners are also heterogeneous systems to which polymer liquid crystals can be added. A liquid crystalline lamellae forms in the continuous phase. These liquid crystalline layers are able to flow under shear and act as lubricants between the different components of the heterogeneous systems such as the solids and other materials in the product. They also stabilize the actives by entrapping the liquid, air or solids particles or droplets in their matrix and preventing them from flocculating and further coalescing (for further explanation see "Effect of Xanthan Gum upon the Rheology and Stability of oil/water Emulsion", *J. Food Sci.*, ibid, 1274).

The delivery vehicles of the present invention can be used in a wide variety of culinary products including, but not limited to, shortening, butter, margarine, frosting and icing, baked (or microwaved) flour- and dough-based products, and in a wide variety of health and personal care items, e.g. skin and hair conditioning lotions such as hand cream or lotions, skin care products, sunscreens, shampoo conditioners, and liquid or solid drug preparations; and in household products such as soaps, detergents.

An additional benefit of the stable polymeric liquid crystal vehicles of the present invention is that they can stabilize heterogeneous systems. The liquid crystals can exist at the interface of a foam, emulsion or dispersion. That is, they can exist at the interface of a liquid/liquid system (emulsion), a solid/liquid system (dispersion) or a gas/liquid or gas/solid system (foam).

The advantage of this invention is the capability of the polysaccharide liquid crystal to encapsulate or trap active ingredients, e.g. perfumes, flavors, antiseptics, colors, nutrients, drugs, vitamins, preservatives, and antimicrobial compounds which are either soluble in the solvent or can act as the solvent of the polymer liquid crystals. These active materials can be evenly distributed throughout compositions by virtue of the ability of the liquid crystal to be microscopically distributed throughout the product as it adsorbs on interface. Yet, since these active ingredients are encapsulated between layers of the liquid crystal, they are storage stable. Oxidation reactions are slowed down, loss due to evaporation is lessened, and reaction with other compounds are also decreased.

DETAILED DESCRIPTION OF THE INVENTION

As used herein, the term "lipid" includes both fat and synthetic fats as well as oils, soaps, long chain fatty acids, or alcohols, surfactants or emulsifiers. Fats and oils are generally recognized to be fatty acid triglycerides which are either naturally occurring in vegetable and animal fats and oils, but also include rearranged or randomized fats and oils and interesterified fats and oils.

As used herein, the term "synthetic fat" refers to any synthetic triglyceride materials and also fat substitutes such as polyol polyesters and polycarboxylic acid esters. These synthetic fats generally act as lipid substitutes in compositions.

As used herein, the term "solid material" refers to any solid food ingredient which is capable of adsorbing onto the polymeric liquid crystal. Solids include starches, modified starches, celluloses, modified celluloses, polydextroses, proteins, solid fats and sugars, soaps, silica, waxy emulsifiers or surfactants such as those used in cosmetics.

As used herein, the term "polysaccharide" refers to a material which is made up of more than ten (10) glucose units in either an alpha (starch) or a beta (cellulose) form or other which is made up of ten (10) monosaccharides, e.g., mannose or mixtures of monosaccharides. These polysaccharides can be chemically modified. Polysaccharides are described in detail below.

The stable polymeric liquid crystal comprises a solvent, preferably a polar solvent like water, and a polysaccharide (hereinafter referred to interchangeably as the "liquid crystal polymer") present at the appropriate relative concentration level such that the liquid crystalline state is substantially one phase and is a polymeric liquid crystalline state. A variety of polysaccharides can be used including extracellular gums and cellulosic derivatives. The liquid crystal polymer can have a wide range of molecular weights, typically between about 500 and about 1,000,000. An average molecular weight of between about 750 and about 200,000 is preferred, between about 1,000 and about 100,000 being more preferred. The molecular weight of the polysaccharides as used herein is an average molecular weight. In addition to the molecular weight, the viscosity can be used to characterize the polymer.

The polymer must also be sufficiently soluble in the solvent such that a liquid crystalline state can be formed at the temperature conditions of the product preparation will be made and, in the typical case, use conditions. Additionally, the liquid crystal polymer should be of a type which has the capability to flow under application of shear. Without necessarily limiting the invention, it is believed that the preferred polymers form cholesteric liquid crystals.

By "active" herein is meant the material which is being encapsulated or delivered by the polymer liquid crystals. Active includes nutrients, minerals, health care ingredients, flavors, perfumes, drugs, e.g., antibiotics, antimycotic, virucides, bacteriocides, protective agents such as sunscreens, vitamins and other physiologically active materials.

1. Polymeric Polysaccharide Liquid Crystal

The polymeric polysaccharide liquid crystal component comprises solvent and polysaccharide polymer. When the materials are used in foods both the solvent and the polysaccharide need to be edible. In general, the polysaccharides useful for the present invention are soluble in the solvent and form lyotropic mesophases, i.e., form anisotropic states in solution) characterized by the alignment of molecules. Because the molecules are aligned, they flow one over the other and thus the liquid crystals flow under application of shear. Liquid crystals are easily oriented by surfaces, electromagnetic files and mechanical stress or shear. The degree of orientation affects their viscosity. The rheological behavior of a liquid crystal is known to be dependent on both the nature and texture of the mesophase.

Many of the polysaccharides used herein form cholesteric liquid crystals. However, the scope of the present invention is not limited to liquid crystals that can be verified as specifically falling into the cholesteric category. Rather, flowable polymeric polysaccharide liquid crystals which meet the chemical and analytical requirements set forth herein are encompassed by this invention.

In general, polysaccharides which form liquid crystals are characterized as having rigid or semi-rigid backbones. See, for example, P. Weigel et al., incorporated herein by reference above, and F. Fried and P. Sixou, "Lyotropic Mesophases of Hydroxypropylcellulose in Pure Acetic Acid, in Water, and in Mixed Solvents," *J. of Polymer Science & Polymer Chemistry Edition*, Vol. 22, 239–247 (John Wiley & Sons, Inc., 1984). not intended, however to necessarily limit the invention by type of polysaccharide polymer backbone, or to necessarily exclude polymers with flexible backbones.

A. Polysaccharide Polymer

A variety of polysaccharide polymers can be used. The polymers can have molecular weights of from about 500 to about 1,000,000; however, lower molecular weight polymers within the range of about 750 to about 500,000 are preferred, and those with molecular weights of between about 1,000 and about 60,000 are more preferred.

Polysaccharides useful for the present invention include a wide variety of polysaccharides, including polyglucose materials, gums, hydrocolloids, cellulose and cellulose-derivative polymers. Gums are plant or microbial (extracellular polysaccharides) derived materials which are modified polysaccharides, but which have achieved their own terminology in the art. Many of these and other suitable polysaccharides are described in more detail in *Industrial Gums—Polysaccharides and Their Derivatives*, Roy L. Whistler, editor, Academic Press (New York), 1959, incorporated by reference herein, and also in P. Weigel et al., "Liquid Crystalline States in Solutions of Cellulose and Cellulose Derivatives," Acta Polymerica, Vol. 35, No. 1, 1984, pp. 83–88, also incorporated by reference herein.

Useful polysaccharides include nonionic, anionic and cationic polysaccharides. Preferred nonionics include the hydroxypropyl cellulose polymers known as the KLUCEL series available from Hercules, Inc. of Naplesville, Ill., USA and xanthan gum available from Kelco, San Diego, Calif. Some preferred anionic polymers are the sodium alginates (commercially available from Kelco) and sodium carboxymethylcellulose polymers available from Hercules. Some preferred cationic polymers are Chitosan™ and Chitin™ from Protan, Inc., Redmond, Wash. These cationic materials are not yet approved for food use. Depolymerised guar, e.g. T4406 (Hi Tek Polymers Inc., Clifton, N.J.), is also useful.

B. Solvent

The solvents useful for the polysaccharide liquid crystals of the present invention include any solvent acceptable for human ingestion which is capable of dissolving the polysaccharide. Preferably the solvent is a polar solvent. Suitable solvents include: water; low molecular weight carboxylic acids, e.g. acetic acid, propionic acid, butyric acid; medium and long chain saturated and unsaturated carboxylic acids, e.g. linoleic acid, decanoic acid, oleic acid; alcohols, such as ethanol, propyl alcohol, isopropyl alcohol, hexanol, and benzyl alcohol; polyols, such as propylene glycol and glycerine; flavor oils, and mixtures thereof. Water and water mixtures of these solvents are preferred.

Flavor oils such as peppermint oil, orange oil, citrus oil, wintergreen oil can be used. Flavor oils are usually mixed in a solvent such as ethanol to dilute the flavor. The flavor oils useful herein can be derived from natural sources or be synthetically prepared. Generally flavor oils are mixtures of ketones, alcohols, fatty acids, esters and terpenes. The term "flavor oil" is generally recognized in the art to be a liquid which is derived from botanical sources, i.e. leaves, bark, or skin of fruits or vegetables, and which are usually insoluble in water.

Additionally, the solvents utilized to form polysaccharide liquid crystals can optionally have other soluble additives, including: salts, e.g., sodium chloride and potassium chloride; nonpolymeric saccharides such as mono-, di-, and oligosaccharides, e.g., honey, sucrose, and fructose; flavors; food colors; vitamins; minerals; drugs; preservatives; or other components in amounts safe for human ingestion. It is often desirable to incorporate lower molecular weight sugars, dextrins, polydextroses and polyols such as glycerine and propylene glycol into the cholesteric liquid crystal solvent in order to lower water activity and, consequently, increase shelf life of the polymer liquid crystal-containing compositions. Suitable additives include sucrose, fructose, glucose, lactose, maltose, maltrin, dextrins, polydextrose and mixtures thereof in liquid or solid form. The level of salts and sugars which can be added is within the skill of one in the art. Too much salt or sugar can interfere with the ability of the solvent to solubilize the polymeric polysaccharide and thus, to form the liquid crystal.

An emulsifier or surfactant can also be added to the polymer liquid crystals. This eases the preparation and lowers the onset of the one phase liquid crystal region. The emulsifier is in addition to the solvent. Suitable emulsifiers include polyglycerol esters, monoglycerides, and sucrose monoesters.

The following tables indicate approximate one phase. cholesteric liquid crystal concentrations for exemplary combinations of polysaccharides and solvents. These ranges are illustrative and can vary depending on a variety of factors, as disclosed herein.

Mixtures of polysaccharides can also be used. For example, 47% of Klucel makes a single phase polymeric liquid crystal. When you add 5% xantham to 25% Klucel, the onset of the one phase liquid crystallinity region is lowered. One can determine which mixtures function well without undue experimentation.

TABLE I

| Polysaccharide | Solvent at 30° C. | Approx Single Phase Liquid Crystal Concentration range wt. % polysaccharide based on total liquid Crystal Weight - Range |
|---|---|---|
| Sodium Carboxy-methylcellulose (D.S. = 1.74)[a] | water | 40%–60%[a] |
| Sodium Carboxy-methylcellulose (D.S. = 1.74)[a] | 2% aqueous NaCl | 50%[a] |
| Ethyl Cellulose (Hercules, Inc.) T-10 D.P. = 110) D.S. = 2.5[+])[a] | $CH_3COOH$ | 50% (40–60)[a] |
| Hydroxypropyl Cellulose (KLUCEL G, Hercules, Inc. D.P. = 750)[a] | water | 30%–50%[a] 47–70* |
| *Hydroxypropyl Cellulose (KLUCEL E M.S. = 3.0) | water | 47%–70%* 41%–60%[b] |

[a] Values obtained from French Patent Publication 2,340,344, Manuel Panar and Oswin Burr Willcox published February 9, 1977.
*Values obtained from G. Conio et al., Macromolecules, 16, (8), 1264 (1983)
[b] R. S. Werbourwyji and D. G. Gray, Macromolecules 13, 69 (1980). Approx single phase liquid is the onset of birefrigence under polarized light microscopy. It can be the beginning of the two phase (biphase), i.e. liquid crystals and isotropic phase. Werbowyj and Gray reported the onset of one phase at 41%. Conio found the beginning biphasic at 39%–47% and beginning one phase at 47% to 80%. Birefringence begins at 41% for Klucel E.

Preparation of the Liquid Crystal

Formation of the liquid crystalline state and the concentration at which such liquid crystalline state occurs is dependent upon a variety of factors, including the specific types of polysaccharide, solvent, temperature, solubility of the polysaccharide in the solvent, and concentration of the polysaccharide. Characteristics of the polysaccharide which can affect the concentration level at which cholesteric liquid crystals form include the degree and type of substitution and molecular weight. The liquid crystals of the present invention can be prepared by combining the polysaccharide and solvent together in the proper ratios. Formation of the cholesteric liquid crystalline state is accelerated by mechanical agitation. Mixing, can be performed either by hand (i.e., using hand utensils) or with mechanical equipment useful for home, institutional, or industrial food or cosmetic preparation. A dough mixer, often referred to as kneaders is useful. Other applicable mixing equipment includes Planetary mixers and Hobart mixers. Extruders which provide a shearing operation with mixing can be used.

Generally polysaccharide liquid crystals are formed at room temperature or ambient temperatures. The processing temperature will depend somewhat on the properties of the solvent. However, processing temperatures in the range of 10° C. and 50° C. are used. For hydroxypropyl cellulose, this temperature range is from 25° C. to 45° C.

The onset of liquid crystal formation is characterized by a decrease in the viscosity of the mixture. As concentration of the polymer is increased, the composition will eventually form an essentially one phase liquid crystal composition. At higher concentrations a solid phase is formed. At higher concentrations and higher temperatures additional phases, such as gel and/or solid phases, can form in addition to or the exclusion of the liquid crystal base. However, it is the one phase liquid crystal which is desired for the purposes of this invention, and quantities and percentages of liquid crystal, as used herein, shall refer to a one-phase liquid crystal component of any composition.

Separation of the liquid crystal phase from excess liquid (solvent or solution) or solid may be achieved by ultracentrifugation. Ultracentrifugation should be conducted using sufficiently high centrifugal forces (preferably within the range of about 20,000 rpm to about 60,000 rpm) to induce the formation of observable phase boundaries for a long period of time (see Conio et al.) Under these conditions a good separation of isotropic and anisotropic phases is obtained. The volume of each phase is determined by calibration of the centrifuge tube and the volume fraction of isotropic phase thus calculated.

At certain concentration ranges spherulites can be formed, particularly with xanthan and hydroxypropyl cellulose). These are concentric droplets which may be used to encapsulate materials. They are cholesteric liquid crystals.

MIXING WITH OTHER MATERIALS

Water

Water can dilute polysaccharide liquid crystals out of its liquid crystalline phase into the isotropic phase. For example, the onset of a one phase liquid crystalline Klucel E is about 47% Klucel in water (Conio, et al., Macromolecules, 16, (8), 1265 (1983).) Adding more water to 47% Klucel E liquid crystals will shift the concentration towards the biphasic system of liquid crystals and isotropic solution (39% to 47%). Increasing the water, even more will lead to the isotropic phase. Thus, only concentrated liquid crystals can be diluted within their liquid crystalline phase boundaries.

Oil

Liquid crystals have to be mechanically dispersed in liquid oil using a micro-fluidiser, mixers, etc. Such systems have the advantage that water is dispersed in the oil through the liquid crystals, i.e., water is not available to separate upon standing as in an emulsion. It is part of the liquid crystalline system.

Solid Components

Solids, such as starch, flour, sol id fat, proteins, silica, soap, emulsifiers, surfactants, long chain alcohols or acids etc., mix with polysaccharide liquid crystals to make an essentially homogeneous mix. Under polarized light microscopy a sample of polysaccharide liquid crystals and modified starch appears homogeneous. In other cases, there is no apparent difference between the control (liquid crystals) and the sample containing liquid crystals. Examples of such mixtures include solid fats and peanut butter. Care has to be taken in certain cases that the solid does not compete with the polysaccharide for its water. An example of such a behavior is if a polysaccharide liquid crystal is added as such to defatted peanut protein, the liquid crystals break down. To avoid such a behavior and to stabilize liquid crystals, sugars, polyols or humectants are dissolved in the water from which the liquid crystals are formed. Then the polysaccharide liquid crystals are added to the protein. The presence of molasses, honey or sugars in the system can be an alternative solution to prevent such a competition for the water between the protein and the polysaccharide. Other humectants can also be used.

The addition of such polysaccharide liquid crystals can change the texture, rheology and functionality of those compounds.

The polymeric liquid crystal can be formed separately, and the active added to it or the active can be added to the mixture when the liquid crystal is formed.

Preparation of Stable Polymeric Liquid Crystal Delivery Vehicle

Preferably the active is dissolved in solvent and the solvent and solute added to the polymer to form the liquid crystals. However, as noted above certain actives can act as solvents. Any conventional mixing technique can be used, including extrusion to mix the actives in. The solvent and solutes are mixed-with the polymer until the combination appears to be an homogeneous solution.

An alternative method of preparing the liquid crystal is to mix the polysaccharide and the active and then add the solvent. The stable polymeric liquid crystal will encapsulate the additive. The same types of agitation and shearing mixing are needed as to form the polymeric liquid crystal. Equilibration may take time.

Actives

The actives used herein include both edible oils and perfume oils. Natural oils are normally extracted from their plant material or animal source by steam distillation and without any dilution in a solvent or carrier. Artificial or synthetic forms of natural oils can also be used. Oils which are extracted from the plant or animal source, rather than those removed by steam distillation, can also be used herein. These edible or essential oils are obtained from various parts of the plant, e.g. leaves, fruit, bark, root, grass, wood, heartwood, gum, berries, seed, flowers, twigs and buds.

Edible oils are used to provide both flavor and aroma to food products, toothpaste, mouthwash, as well as to soaps and detergents. They may also be added to drugs and other skin creams or lotions to provide a pleasant aroma or to mask the aroma of the drug or other active used in the cream or product. Usually they are dissolved in glycols or alcohols, e.g. benzyl or ethyl alcohol or propylene glycol.

Preferred oils for use herein include almond, anise, camphor, caraway, cassia, cedar leaf, cedar wood, cinnamon, citronella, clove, eucalyptus, geranium, grapefruit, lavender, lemon, lemon grass, rose oil, lime, orange flower (neroli), nutmeg, onion, garlic, orange, riganum, oris, peppermint, pine, pine needle, rosemary, sandlewood, sassafras, spearmint, thyme, coffee, tea, cherry, apple, pineapple, banana, peach and vanilla.

Nutrients can also be used as actives. These include minerals such as calcium, manganese, iron, zinc, copper, sodium and potassium. These minerals may be added as water soluble salts or other bioavailable forms. Particularly preferred is calcium citrate malate and iron sugar carboxylates. These are disclosed in U.S. Pat. No. 4,786,510 and U.S. Pat. No. 4,786,518. In addition, other nutrients include both water soluble and oil soluble vitamins and vitamin precursors. These include vitamins A, E, the B vitamins, including riboflavin, beta-carotene, vitamin C and D.

Sunscreens such as PABA can also be encapsulated by this technique. Other actives for example antiseptics such as bacitracin, bacteriocides, virucides, alcohol, merthiolate, iodine and iodine solutions, alcohol, trichlorcarban, aspirin, antihistamines, tetracyclines and other topical drugs or agents can also be used as actives in this invention. Antioxidants such as butylhydroxytoluene, butylhydroxyanisol, ascorbic acid and similar compounds can be used.

Drugs can also be encapsulated. These include aspirin, ibuprofin, acetometaphen, antitussives, tetracyclines, and other analgesic agents.

Identification of Liquid Crystals

Those skilled in the area of flowable lyotropic, polymeric liquid crystals will be able to identify cholesteric liquid crystals based upon known identification techniques.

As discussed in detail above, liquid crystal formation for any particular polymer and solvent combination is readily identified using one or more of several identification techniques. The onset of liquid crystal formation and the occurrence of a substantially one-phase liquid crystal state for a particular polymer and solvent system can be identified by: (1) visual observation with the naked eye, (2) birefringent optical activity observed by light microscopy; and/or (3) measurement of the polymer/solvent system NMR spectra; (4) measurement of apparent viscosity profile described in more detail below); and (5) presence of a characteristic "texture" pattern observable under polarized light microscopy.

A general description of liquid crystalline structures includes the physical structure on a molecular scale, which is characterized by positional as well as orientational order of neighboring molecules and the supermolecular arrangement of assemblies of molecules or parts of molecules. The supermolecular structure, which is often called the morphology, is exclusively called the texture in the case of liquid crystalline phases. The molecular structure and the texture of a mesophase determine its physical and technological properties. Observed textures are directly related to the material's molecular structure. It may be possible to derive the molecular structure of the liquid crystalline modifications from observations of its textures.

Textures of liquid crystalline phases determine the optical properties of these materials to a great extent. The wide range of applications of these systems depends on the ease with which textural changes and therefore changes in optical properties can be brought about by mechanical, thermal, electric and magnetic forces. The macroscopic orientations of the molecules in the sample determine the textures. In the case of the so-called homeotropic texture, the particles are arranged with their long axes parallel to the film normal throughout the macroscopic sample, whereas in the so-called homogeneous texture, the long axes are oriented parallel to the film surface. Textures of liquid crystalline phases are often studied by using polarizing microscope.

Light microscopy of liquid crystals is described generally in *The Microscopy of Liquid Crystals*, Norman, Hartshorn, London, England and Chicago, Ill., U.S.A., 1974, which discusses birefringence of mesomorphic states and methods for microscopic observation and evaluation (Chapter 1, pp. 1–20, and specifically for cholesteric mesophase systems see Chapter 6, pp. 79–90). Birefringence is a preferred method for determining the occurrence of a liquid crystal for the polysaccharides used herein.

The different textures encountered in liquid crystalline phases will be described in detail. The following part is devoted to the description of the optical character of the textures observed for thin films between glass slides or for thin slices of a material under the polarizing microscope: The orientational order, which determines the textures, is also discussed.

I. In thin film samples of a nematic liquid crystalline material, one observes dark flexible filaments under the optical microscope. These are caused by lines of singularities in the molecular alignment. The term "black filaments" is used for this texture. A characteristic texture of the nematic phase is the "Schlieren texture," which is caused by a nonhomogeneous orientation of the particles of the material. One observes dark brushes that start from point defects in a homeotropic texture, the field of view under the polarizing microscope is black in ideal cases. The optical axes and, consequently, the long axes of the molecules are oriented perpendicular to the plane of the thin films. The optical axes of the molecules are oriented parallel to the plane of the film if the samples exhibit the homogeneous texture. Under the microscope one observes large homogeneous birefringent regions. The nematic marbled texture consists substantially of a great number of nearly homogeneous regions with different orientation of the optical axes.

II. Certain smectic (A and C) modifications also exhibit a focal conic texture. The lamellar structure is due to the smectic layers, thus it is a molecular structure. Smectic structures are not found in the polymeric polysaccharide liquid crystals of this invention.

III. The most characteristic texture of the cholesteric phase is the "planar" texture, which is also called the "Grandjean" texture. It is characterized by the existence of a cholesteric single crystal where the direction of the helical axis is perpendicular to the plane of the film. The pitch of the helical structure, which determines the optical properties of the phase, can be influenced by temperature, additives, or external forces.

Just below the clearing point one may observe a texture in which the helical axis is parallel to the plane of the cholesteric film. One can directly observe the pitch of the helix, provided that it is large enough to be resolved. This texture has been referred to as "fingerprint" texture. In thicker samples the "focal conic" texture is usually obtained. Characteristic of this texture is the occurrence of an arrangement of fine dark lines. The lines form ellipses and hyperbolas or parts of ellipses and hyperbolas. The specific pattern is caused by the existence of a lamellar structure that can be deformed in such a way that the distance between the lamellar planes stays constant. In the case of the cholesteric phase the lamellar structure is due to the helical structure; it is thus a supermolecular structure.

Often observed with the naked eye in cholesteric phases are irridescent colors. The cholesteric phase is characterized by the fact that the direction of the long axes of the molecules change continuously within the samples. This leads to a twist about an axis perpendicular to the long axes of the molecules. If the pitch of the helical structure agrees with the wavelength of the visible light, selective reflection of monochromatic light can be observed. This effect leads to the irridescent colors.

Cholesteric polymer liquid crystals are also characterized by a distinctive viscosity profile as a function of concentration. A polymer/solvent mixture at lower polymer concentration forms an isotropic solution. As the concentration of the polymer increases, the viscosity of the solution first increases until it reaches a maximum viscosity peak; then the viscosity decreases dramatically with further increases of polymer concentration. It is understood by those skilled in the art that maximum viscosity peak signifies the presence of the polymeric lyotropic liquid crystalline order. On the other hand, polymer isotropic gels, polymeric isotropic solutions are characterized by increasing or stable viscosity with increasing polymer concentration. Simple mixtures of solid polymers and solvent do not have this viscosity profile. The changes in the viscosity are due to molecular alignment in the liquid crystal.

Addition of the Stable Polymeric Liquid Crystal to Foods

The stable polymeric liquid crystal can be used in foods as a substitute for fat, or other food ingredient. Preferably from 0.5% to 50% of the fat component can be replaced with the stable polymeric liquid crystal. When the stable polymeric liquid crystal contains water, there may be some adjustment of the recipe or formulation required. Generally food formulations can be adjusted without undue experimentation.

The polysaccharide liquid crystals of the present invention can be incorporated into any edible food which contains a solid material. The liquid crystal should be well mixed with the solid component of the composition. It is preferably to prepare the liquid crystal first, and then mix it with the solid, in order to most effectively achieve a microscopic distribution of the polymeric polysaccharide liquid crystal in said solid.

Starch can also function as the solid to which the fat substitute adsorbs. Starch is composed primarily of glucose and is derived from cereal grains. Common starches include starches derived from potato, wheat, corn, rice, maize, barley, rye and tapioca. Starches are comprised of both amylose and amylopectin. Both types of starches will function herein. Starches which are oxidized, bleached or otherwise modified, including pregelled starches can be used herein. Proteins can also function as the solid.

Shortening Compositions

Preferred solid or plastic fat for use in shortening compositions include hydrogenated and unhydrogenated animal or vegetable oils. Shortenings usually contain from about 1% to about 15% hardstock. Hardstock are triglycerides of long chain saturated fatty acids which have an Iodine Value of 15 or less. Tristearin, tripalmitan and triglycerides of palmitic and stearic acid are preferred hardstocks for use in shortenings. Other fatty acids can be present, usually the hardstock is made of fatty acids having from 12–22 carbon atoms. The triglyceride hardstock comprises from about 75% to about 100by weight of beta tending triglyceride and from 0 to about 25% by weight of non-beta tending triglyceride. Preferably, the triglyceride hardstock is all beta tending triglyceride.

Suitable normally solid triglycerides having strong beta-forming tendencies include, for example, substantially completely hydrogenated triglyceride fats derived from soybean oil, hazelnut oil, lard, linseed oil, olive oil, peanut oil and sunflower seed oil. Substantially completely hydrogenated soybean oil, for example, soybean oil hydrogenated to an iodine value of less than about 10, is a suitable beta-tending triglyceride constituent.

The preferred shortening products of the present invention will contain little or substantially no solvent which is not incorporated into the liquid crystal. Preferably less than 10% of the solvent, based upon the total weight of solvent incorporated into a cholesteric liquid crystal form, is present in the fat products, more preferably, less than 1%, and most preferably, substantially no solvent (defined herein as being less than about 0.5%). While the presence of excess solvent is not preferred for the fat products, the presence of said solvents is still meant to be encompassed in said products, to the extent that the liquid crystal remains phase-stable.

The shortening compositions can also contain a stabilizer to protect against oxidative deterioration at high temperatures, such as increases in viscosity and fatty acid content, formation of polymerized fatty matter, increase in refractive index and destruction of tocopherols and intensification of foaming tendencies due to the formation of oxidized and polymerized constituents. Silicone oils, particularly methyl and ethyl silicones, are useful for this purpose. Suitable viscosities of the silicones are in the range of from about 50 to about 1,000,000, preferably from about 100 to about 1000 centistokes at 25° C. Silicone at a level of 0 to 10 ppm by weight, and 1 to 5 ppm by weight is preferred. Appropriate means must be used to assure substantially uniform dispersion of the small amount of silicone throughout the shortening composition. The silicone preferably is added to the starting material after completion of the refining, bleaching and optional deodorizing processes. Other antioxidants include butylhydroxyanisole and butylhydroxy toluene.

Various other additives can be used in the shortenings of this invention which are edible and aesthetically desirable and do not have a detrimental effect upon the melting and crystallization characteristics of the shortening. The types of additives employed should be consistent with the ultimate end use.

Margarine/Butter

Polysaccharide liquid crystals are effective flavor delivery vehicles for use in emulsified fat spreads, e.g., solid or semi-soft margarines, and butters. The polysaccharides in their liquid crystalline form are homogeneously distributed on a microscopic level in the fat. Thus the absence of macroscopic clumps and particles reduces any inherent polysaccharide slimy taste and grittiness. The liquid crystals can be added to margarines and butters by simply mixing such liquid crystals with the margarine or butter in a softened, but preferably not liquified, state. Such margarine and butter compositions comprise from about 0.5% to about 80% of the polysaccharide liquid crystal, more preferably from about 1% to about 60%.

Any commercially available margarine or shortening can be used in conjunction with polysaccharide liquid crystals. Preferably, the non-dietary formulations, i.e., those without other added fat substitutes, are utilized.

Typically, conventional margarine comprises up to about 20% of an aqueous phase and from about 75% to about 90% of a fat phase, preferably at least about 80%. Spreads or diet products contain from 50% to 80% fat phase and 20% to 50% water.

The aqueous phase usually contains milk or milk solids. The milk component can be derived from whole milk, low-fat milk (about 2% butterfat content), skim milk or nonfat dry milk solids. The amount of milk and/or milk solids (in terms of % by weight solids) usually ranges from about 0.5% to about 5% by weight of the emulsified spread, and more typically from about 1% to about 3% by weight. Particularly where milk solids are used, water, typically in the form of distilled or deionized water, is included as part of the aqueous phase. For a non-browning spread, the milk solids or reducing sugars in them are eliminated.

Other ingredients included within the aqueous phase are flavorants such as salt and other water-soluble flavors.

Usually, salt is included in an amount of from about 0.5% to about 3.5% by weight of the emulsified spread, and more typically in an amount of from about 1% to about 2.5% by weight. The amount of the other water-soluble flavors depends upon the particular flavor characteristics desired.

Another important component of the aqueous phase are the preservatives, for example, citric acid, potassium sorbate and sodium benzoate. The preservatives are added in amounts effective to prevent oxidation, bacterial and mold growth.

Margarine fats are usually made from triglycerides which have predominantly long chain length fatty acids (e.g., palmitic, stearic, oleic and/or linoleic residues). These long chain fatty acid triglycerides can be interesterified to provide margarine fats having different melting profiles. More typically, the long chain fatty acid triglyceride is a hydrogenated (hardened) oil. See *Bailey's Industrial Oil and Fat Products, supra*, at page 339.

Improved margarine fat phases (also useful for other emulsified spreads) are disclosed in U.S. Pat. No. 4,388,339 to Lomneth et al, (1983).

Methods for making and processing margarine are well known in the art and one method is also disclosed in U.S. Pat. No. 4,388,339.

Other ingredients can be present in the oil phase. One particularly important ingredient is the emulsifier. Emulsifiers which can be used include mono- and di-glycerides (water-in-oil stabilizers and baking aids), lecithin (oil-in-water stabilizer, as well as anti-stick and anti-spatter agent), and polyoxyethylene sorbitan monoesters such as TWEEN 60 and TWEEN 80 (oil-in-water stabilizers). Other conventional emulsifiers can also be used. The emulsifiers are added in amounts of from about 0.01% to about 10% by weight of the spread, and preferably in an amount of from about 0.1% to about 0.5% by weight. Coloring agents such as beta-carotene and oil soluble flavors can be in the oil phase. The amount of colors and flavors depends upon the color and flavor characteristics desired and is within the skill of the art.

The polysaccharide liquid crystal is added into the margarine, fat, or other emulsified fat spread by mixing.

Protein-based Polysaccharide Liquid Crystal Adsorption Surface Products

The polymer liquid crystals can be used to deliver flavors, perfumes, drugs, and other actives in a variety of products with solid adsorption surfaces other than, or in addition to, solid fats. These include a variety of protein-containing products for example lotions, sunscreens, enzyme containing detergents, etc.

The present invention, accordingly, further relates to protein-containing compositions which comprise from about 90% to about 10% of a protein component, and from about 2% to about 75% of an edible polysaccharide liquid crystal encapsulating an active. The polysaccharide liquid crystal can be incorporated into the product by mixing it with the protein component.

Toothpastes, cosmetics and soaps all have either a fat, protein or starch base. The same formulations used to add the polysaccharide liquid crystal active vehicles to foods can be used to add them to these materials.

A typical skin cream formulation comprises:

(A) from 0.1% to 10% encapsulated active vehicle (B) from 85% to 99.9% 1 lipids, and (C) from 0.1% to 3% emulsifiers.

A variety of product executions of the present invention are exemplified below. These examples are not meant to define or otherwise limit the scope of the invention. Rather, the scope of the invention is to be ascertained according to the claims which follow the examples.

EXAMPLE I

Preparation of Liquid Crystals

| Ingredient | Amount (% By Weight) |
|---|---|
| Klucel E | 47 |
| Water | 53 |

Liquid crystals are formed by mixing the above ingredients together until the mixture is homogeneous, birefringent under polarized light microscopy and the viscosity changes to a flowable mixture.

EXAMPLE II

Preparation of Fat Substitute

| Ingredient | Amount (% By Weight) |
|---|---|
| Crisco Shortening | 66 |
| Liquid crystal from Example I | 34 |

The liquid crystal from Example I is mixed with the shortening and until a homogeneous blend is made. This shortening is then used in baking.

EXAMPLE III

Preparation of Fat Substitute With Encapsulated Preservatives

| Ingredient | Amount (% By Weight) |
|---|---|
| Klucel E | 15 |
| citric acid | 6 |
| water | 9 |
| shortening | 70 |

The fibers are added to the citric acid, potassium sorbate and water under high shear. When the liquid crystals are formed, the shortening is added and mixed until homogeneous. This shortening substitute is stable to bacterial growth.

EXAMPLE IV

Peppermint flavored liquid crystals are formed in a method similar to Example I from the following materials:

| Ingredient | Amount (% By Weight) |
|---|---|
| Klucel E | 47 |
| Benzyl Alcohol | 26.5 |
| Peppermint Oil | 26.5 |

EXAMPLE V

Calcium, sugar and salt can be encapsulated in liquid crystals for adding to foods and other edibles.

| Ingredient | Amount (% By Weight) |
|---|---|
| Xanthan | 5.26 |
| Sucrose | 47.37 |
| Water | 47.37 |

The sucrose is dissolved in the water and then mixed with the xanthan gum to make a liquid crystal. The maximum ratio of sucrose to water is 1:1. From 0.1:1 to 1:1 sucrose to water can be used.

Maltose can also be used. 54.03% water and 40.71% maltose is used to replace the sucrose and water.

| Ingredient | Percent |
|---|---|
| Calcium Chloride | 5 |
| Xanthan | 10 |
| High Fructose Corn Syrup (69% solids) | 85 |

Calcium citrate malate can be used instead of the calcium chloride.

| Ingredient | Percent |
|---|---|
| Xanthan | 8 |
| Calcium Citrate Malate | 2 |
| High Fructose Corn Syrup | 90 |

EXAMPLE VI

Triclocarban is encapsulated in a liquid crystal prepared as in Example I. This is then added to a soap solution to make a bar soap.

| Ingredient | Amount (% By Weight) |
|---|---|
| Klucel E | 50 |
| PEG 350 | 45 |
| Triclocarban | 5 |

EXAMPLE VII

A water soluble formulation of 2-phenylbenzimidazole-5-sulfonic acid (Eusolex 232) is encapsulated with water (37%) and Klucel E (HPC, 47%). The level of Eusolex is 16%. This is then added to a cream base to make a sunscreen lotion.

EXAMPLE VIII

Triclosan (10% is encapsulated in a liquid crystal prepared by mixing it with 50% Klucel and 40% propylene glycol.

What is claimed is:

1. A topically applied cosmetic composition comprising an:
   (a) from about 0.001% to about 60% of an active ingredient; and
   (b) from about 40% to about 99.999% of a stable polymeric liquid crystal consisting essentially of:
      (1) from about 10% to about 90% of a solvent; and
      (2) from about 10% to about 90% of a polysaccharide having a molecular weight of from about 500 to about 1,000,000.

2. A composition according to claim 1 wherein said solvent is a polar solvent.

3. A composition according to claim 2 wherein said active ingredient is selected from the group consisting of drugs, sunscreen, vitamins and minerals.

4. A composition according to claim 3 wherein said solvent is selected from the group consisting of water and alcohols.

5. A composition according to claim 4 wherein said polysaccharide has a molecular weight of from about 2500 to about 1,000,000.

6. A composition according to claim 3 wherein said polysaccharide is selected from the group consisting of substituted cellulose, cellulose-derivative polymers, gums, hydrocolloids and polyglucose materials.

7. A composition according to claim 6 wherein said polysaccharide is selected from the group consisting of methyl cellulose, ethyl cellulose, ethyl hydroxyethyl cellulose, hydroxypropyl cellulose, sodium carboxymethyl cellulose, hydroxypropylmethyl cellulose, ethylmethyl cellulose, guar gum derivatives, xanthan gum, psyllium gum, alginate, locust bean gum and mixtures thereof.

8. A composition according to claim 7 wherein said polysaccharide is selected from the group consisting of methyl cellulose, hydroxypropyl cellulose, xanthan, alginates, and mixtures thereof.

9. A composition according to claim 1 wherein said solvent is selected from the group consisting of alcohol or glycol mixtures of flavor oils and perfume oils.

10. A composition according to claim 9 wherein said flavor oils are selected from the group consisting of peppermint oil, clove oil, spearmint oil, orange oil, citrus oil, butter oil and mixtures thereof.

11. A composition according to claim 10 wherein said solvent is a perfume oil with alcohol or glycols.

12. A composition according to claim 1 which is a skin cream.

13. A topical skin cream composition comprising:
   (A) from 0.1% to 10% encapsulated active ingredient vehicle comprising:
      a) from about 0.001% to about 60% of an active; and
      b) from about 40% to about 99.999% of a stable polymeric liquid crystal consisting essentially of:
         (1) from about 10% to about 90% of a solvent; and
         (2) from about 10% to about 90% of a polysaccharide having a molecular weight of from about 500 to about 1,000,000;
   (B) from 85% to 99.9% lipids, and
   (C) from 0.1% to 3% emulsifiers.

14. A composition according to claim 13 wherein said solvent is a polar solvent.

15. A composition according to claim 14 wherein said active ingredient is selected from the group consisting of drugs, sunscreen, and perfumes.

16. A composition according to claim 15 wherein said solvent is selected from the group consisting of water and alcohols.

17. A composition according to claim 16 wherein said polysaccharide has a molecular weight of from about 2500 to about 1,000,000.

18. A composition according to claim 17 wherein said polysaccharide is selected from the group consisting of substituted cellulose, cellulose-derivative polymers, gums, hydrocolloids and polyglucose materials.

* * * * *